(12) United States Patent
Vilsmeier et al.

(10) Patent No.: US 9,486,295 B2
(45) Date of Patent: Nov. 8, 2016

(54) UNIVERSAL IMAGE REGISTRATION INTERFACE

(75) Inventors: Stefan Vilsmeier, München (DE); Thomas Bauch, Bergkirchen (DE); Uli Mezger, München (DE)

(73) Assignee: Brainlab AG, Feldkirchen (DE)

( * ) Notice: Subject to any disclaimer, the term of this patent is extended or adjusted under 35 U.S.C. 154(b) by 2028 days.

(21) Appl. No.: 11/677,238

(22) Filed: Feb. 21, 2007

(65) Prior Publication Data

US 2007/0238961 A1 Oct. 11, 2007

Related U.S. Application Data

(60) Provisional application No. 60/743,688, filed on Mar. 23, 2006.

(30) Foreign Application Priority Data

Feb. 21, 2006 (EP) .................................... 06003497

(51) Int. Cl.
*A61B 90/00* (2016.01)

(52) U.S. Cl.
CPC ........ *A61B 90/39* (2016.02); *A61B 2034/2068* (2016.02); *A61B 2090/3954* (2016.02); *A61B 2090/3983* (2016.02)

(58) Field of Classification Search
USPC ........................................ 600/407, 414, 426
See application file for complete search history.

(56) References Cited

U.S. PATENT DOCUMENTS

| | | | |
|---|---|---|---|
| 4,802,109 A * | 1/1989 | Machida ....................... | 708/290 |
| 5,628,315 A | 5/1997 | Vilsmeier et al. | |
| 5,828,774 A * | 10/1998 | Wang ............................ | 382/128 |
| 5,971,997 A | 10/1999 | Guthrie et al. | |
| 6,298,262 B1 * | 10/2001 | Franck et al. ................ | 600/426 |
| 6,662,036 B2 * | 12/2003 | Cosman ........................ | 600/411 |
| 6,772,002 B2 | 8/2004 | Schmidt et al. | |
| 2001/0007918 A1 | 7/2001 | Vilsmeier et al. | |
| 2001/0039421 A1 | 11/2001 | Heilbrun et al. | |
| 2003/0187351 A1 | 10/2003 | Franck et al. | |
| 2004/0145367 A1 * | 7/2004 | Duerk et al. .................. | 324/307 |
| 2004/0167654 A1 | 8/2004 | Grimm et al. | |
| 2005/0109855 A1 | 5/2005 | McCombs | |
| 2005/0228256 A1 | 10/2005 | Labadie et al. | |

FOREIGN PATENT DOCUMENTS

EP 1208808 B1 5/2002
WO 2004/100767 11/2004

* cited by examiner

*Primary Examiner* — Joseph M Santos Rodriguez
(74) *Attorney, Agent, or Firm* — Tucker Ellis LLP

(57) ABSTRACT

A reference structure for use with a medical navigation system, includes an imaging structure, and a plurality of artificial markers arranged at predetermined locations on said imaging structure. The artificial markers are detectable by the medical navigation system, wherein the artificial markers have a known relationship to the imaging structure.

10 Claims, 4 Drawing Sheets

UNIVERSAL IMAGE REGISTRATION INTERFACE

RELATED APPLICATION DATA

This application claims priority of U.S. Provisional Application No. 60/743,688 filed on Mar. 23, 2006, which is incorporated herein by reference in its entirety.

FIELD OF THE INVENTION

The present invention relates to a device and method for supporting the treatment of a patient by means of a navigation system and, more particularly, to a reference structure and method for generic and universal interface with any third party IGS system.

BACKGROUND OF THE INVENTION

Navigation systems detect and track positions of patients, parts of the patient's body, regions to be treated, as well as positions of treatment devices. This information (e.g., images, numerical data, textual data, etc.) then may be displayed on a monitor or the like, and a surgeon may use the images to support treatment. In order to correctly and accurately show the images to the surgeon, the images are correlated with the actual patient space, and this process is called registration.

The idea of feature or object based matching based on, say, fiducials or anatomical landmarks to register a patient can be found in nearly all image guided surgery products. These methods basically utilize 'easy-to-identify' structures in the image set of the patient (usually MR or CT based tomography images) and 'easy-to-reach' structures rigidly attached to the patient. These structures enable the image set space to be correlated with the actual patient orientation in the operating room.

'Easy-to-identify' structures in image sets are usually, but not restricted to, spherical markers or rods that provide high image contrast. The markers typically are attached to the patient in such a way that they are also 'easy-to-reach' with a tracked instrument of the image guided surgery (IGS) system. The quality of the registration, however, depends on the expertise of the person (e.g., his expertise in applying the right number of markers or rods in the right configuration, and the individual setup of the patient bedding, which may limit access to markers or rods). It is not always guaranteed that structures are 'easy-to-identify', because they can be ambiguous, and corresponding structures are not always 'easy-to-reach', because of the patient bedding and specific operating room setup, e.g., drapes, tubes, etc. Hence, consistent registration quality using conventional feature or object based matching, especially when based on fiducials such as registration markers, is not guaranteed.

Such manual registration methods, in comparison to automatic registration methods, usually require a significant amount of time to attach and identify the registration markers and, therefore, such methods may not be feasible for intraoperative use. On the other hand, a disadvantage of automatic registration methods is that they are proprietary and require strong integration in the navigation software.

In contrast, standard paired-point matching image registration, one embodiment of feature or object based matching, is available with typically any commercially available IGS system. In this case, however, accuracy might be low and one needs to access the patient anatomy for image registration. This is typically not possible for the registration of intra-operatively acquired images, because the patient anatomy is not accessible due to draping, etc.

The registration of intraoperative images directly affects navigation systems. For example, problems may arise in the course of treatment if, during treatment, the tissue is subjected to shifting, as may happen, for example, due to liquid discharge or removal of tissue. In such a situation (e.g., if the target of treatment or the surrounding tissue together with the target of treatment has been shifted), the supporting navigation may become inaccurate. As a result, the surgeon can only rely on his own observations or, if he did not notice the shift, he may operate at wrong positions.

A method for supporting the treatment of a patient is described in US 2001/0007918 A1.

SUMMARY OF THE INVENTION

The present invention provides a device and method for generic and universal interface with any third party IGS system, thereby enabling easy registration using pre- and/or intraoperative patient data, without the need of accessing the anatomical structures of the patient and/or the need of any software modifications to the proprietary IGS system.

The automatic image registration method is a straightforward method to register pre- and intraoperative images with high accuracy, without accessing anatomical structures of the patient and without manual identification of scan or registration markers. This advantage is achieved by providing proprietary hardware and software and implementing specific software algorithms for marker detection and coordinate transformation into the navigation software. The image registration information is thus available for the proprietary image format.

A generic interface can be provided for any third party IGS system to easily register pre- and intraoperative patient data without the need of accessing the anatomical structures of the patient and the need of any software modifications to the third party IGS system. The output of the generic interface can be an image set in standard image format (e.g., DICOM) with fixed drawn-in registration markers that can be easily identified by any third party IGS system using, for example, paired-point-matching registration.

The advantages using such a registration structure and methodology include:
registration quality does not depend on user expertise;
reliable due to redundant information;
independent of patient bedding;
consistent registration quality;
guaranteed 'Easy-to-identify' structures in images;
guaranteed 'Easy-to-reach' structures for registration;
time efficient, since only the minimal amount of points need to be identified using a tracked instrument;
requires no explicit software integration into existing IGS systems;
customer can use one hardware for different proprietary IGS; systems; and
allows intraoperative registration.

Further advantages may be based on the fact that, in addition to the data record that the navigation system has used up to that moment, one or several further current patient data records can be created. These additional patient data records can be created either automatically or on demand by an image-generating method, and each current data record can be integrated into the navigation system in a computer-aided manner. Thus, it is not only ensured that a new and current data record, recording the cited tissue shifts and changes, is available at a given time, but the current data record can be simultaneously linked or integrated into the navigation system. This enables the surgeon to perform his work in a time efficient manner with the assistance of precisely integrated and updated navigation support. Accordingly, incorrect treatment can be avoided, and the surgeon no longer has to depend on visually perceiving large-scale tissue removal or liquid discharge.

The additional data records of the patient can be created during the operation by means of different methods. These may be, for example, magnetic resonance tomography (MR), computer tomography (CT) or SPECT/PET methods.

A reference structure can be positioned at the patient or in the surrounding area of the target of treatment, while the current data record is being created. The reference structure can include artificial markers, e.g., notches or other structures that can be detected by the proprietary navigation system (e.g., by pointing at them with a tracked instrument as well as markers that can be detected by the image-generating method, the assignment of data for the markers resulting in a positional integration of the current data record into the navigation system). Alternatively, the reference structure may include markers detectable in the navigation system by pointing directly at the markers with a tracked instrument as well as by the image-generating method.

An artificial marker as used herein is any structure or identifiable element that can be used to identify a position of an object in three-dimensional space, e.g., by using a trackable pointer pointing sequentially at the artificial markers.

Accordingly, the reference structure and the notches or artificial markers thereof are the point of intersection for the assignment of the current data record into the navigation system. Due to the positional detection of the artificial marker, e.g., by pointing at several notches, the navigation system knows the position of the reference structure and, furthermore, its position is known in the newly created data record, as here markers are also detected at the reference structure. Similarly, the image-generating system also knows the position of the pixels and can detect/compensate for deviations between the individual data records of the patient (caused by different positions of the patient) and/or transmit them to the navigation system. Thus, each subsequent data record is automatically referenced. Only the first data record has to be localized/referenced, provided that the patient is firmly fixed, e.g., by means of a rigid head fixation device or the like.

Alternatively, the device for performing the image-generating method may be referenced by the navigation system while the current data record is being detected by means of artificial markers provided thereon. The artificial markers may be detected by the navigation system, and the position of the current data record is thus integrated. This method is similar to the method described above. However, the artificial markers are not provided at the patient or near the patient, but directly at the device for performing the image-generating method, e.g., directly at a mobile MR device that is brought into the operational theater to update data records.

The navigation system knows from the artificial markers or notches where in the region the device for performing the image-generating method is positioned at the moment the new images have been created. This allows the position of the new images to be computed.

BRIEF DESCRIPTION OF THE DRAWINGS

The forgoing and other features of the invention are hereinafter discussed with reference to the drawing.

DETAILED DESCRIPTION

Figure 1:
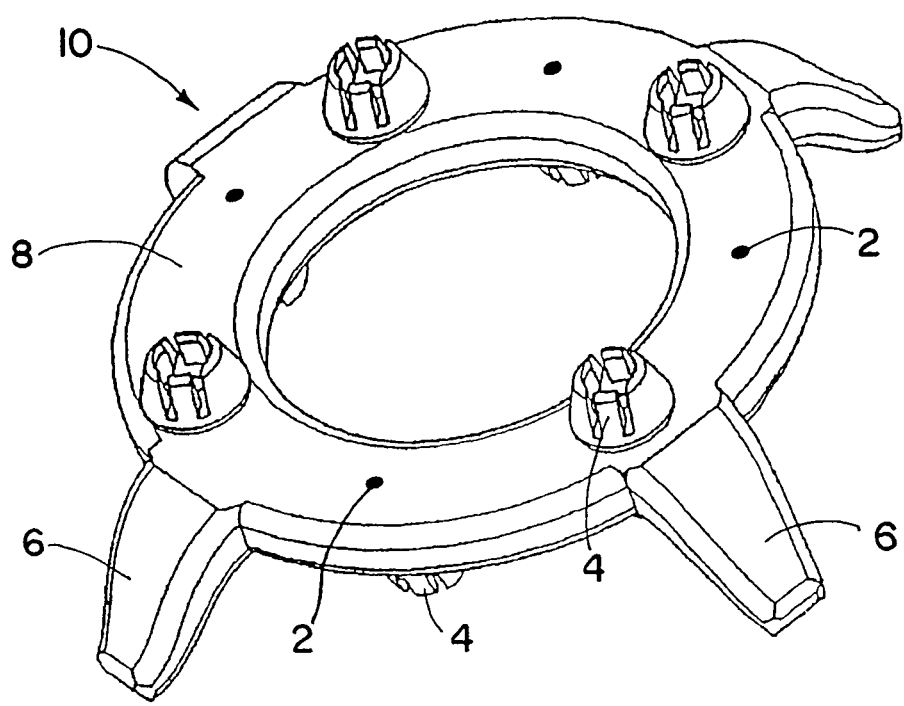
FIG. 1 an exemplary reference structure in accordance with the invention.

FIG. 1 shows an exemplary reference structure 10 that may be used to integrate a position of an updated data record into a navigation system. In this embodiment, the reference structure 10 comprises a carrier ring 8 with arms 6. The carrier ring 8 includes artificial markers, for example notches 2, as well as fixtures 4 for MR or CT markers (not shown), which may be visible in a magnetic resonance or computer tomographic image. These fixtures 4 can be provided on both the top and the bottom side of said ring 8 to receive ball-shaped MR/CT markers therein. It can be assumed that all conceivable tracking systems can be used within the scope of the present invention, including those comprising actively radiating markers, magnetic systems or systems based on ultrasonics. MR or CT visible markers or structures of different shapes also may be used, e.g., rods, flat or cornered markers, etc.

The use of the exemplary reference structure 10 will now be explained in detail with regard to the course of a treatment using navigation updating.

First of all, a diagnostic image data record of a patient is created, e.g., a magnetic resonance or computer tomography data record. Then, the patient may be moved into the operating theater where, in advance, the first data record may again be adjusted by means of known adjusting methods so as to obtain a correctly referenced initial data record that may be used for navigation.

Now, the surgeon may perform an image-guided operation with the assistance of the navigation system. Should the surgeon find out during the course of the operation that a great amount of liquid has already been drained off from tissue or that tissue has already been removed to the extent that inaccuracies may occur in the navigation system due to the shift of tissue, he can activate the intra-operative navigation update. To do so, the patient, first of all, may be covered with sterile cloth. If the operation is to be performed in the region of the head, a sterilized reference structure 10 can be placed, for example, on the patient's face, and then the generation of the current data record may be started. To do so, a mobile MR or CT device, for example, may be moved into the operating theater and positioned beside the patient's head. Alternatively, an already integrated MR or CT within the operating theater may be used.

Figure 2:
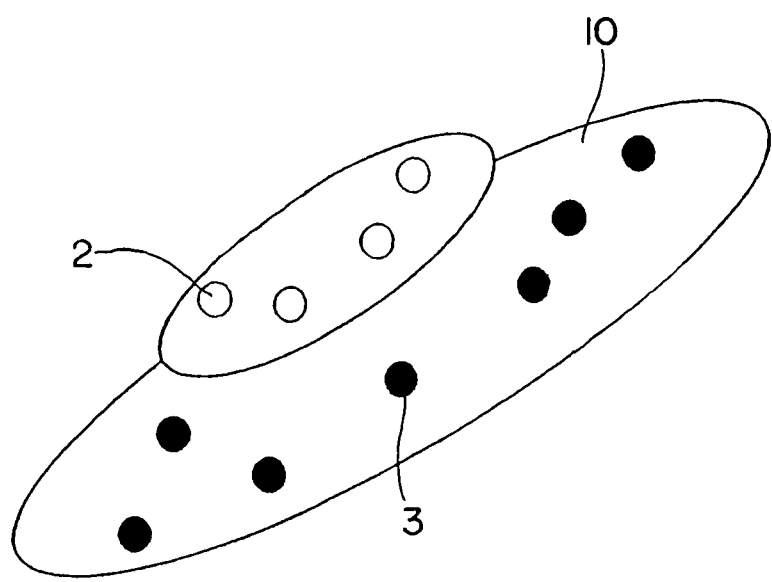
FIG. 2 is an abstract model of the reference structure shown in FIG. 1.

In the case of an intra-operative MR/CT scan, the MR/CT markers 3 of fixtures 4 are also scanned. The hardware module is shown in FIG. 2 as an abstract embodiment of the registration structure of FIG. 1. The hardware module includes an array of unambiguously arranged, 'easy-to-detect' spherical markers 3 and an array of 'easy-to-reach' notches 2. The relation between the registration structure markers 3 and the notches 2 is known either by construction or measurement.

Figure 3:
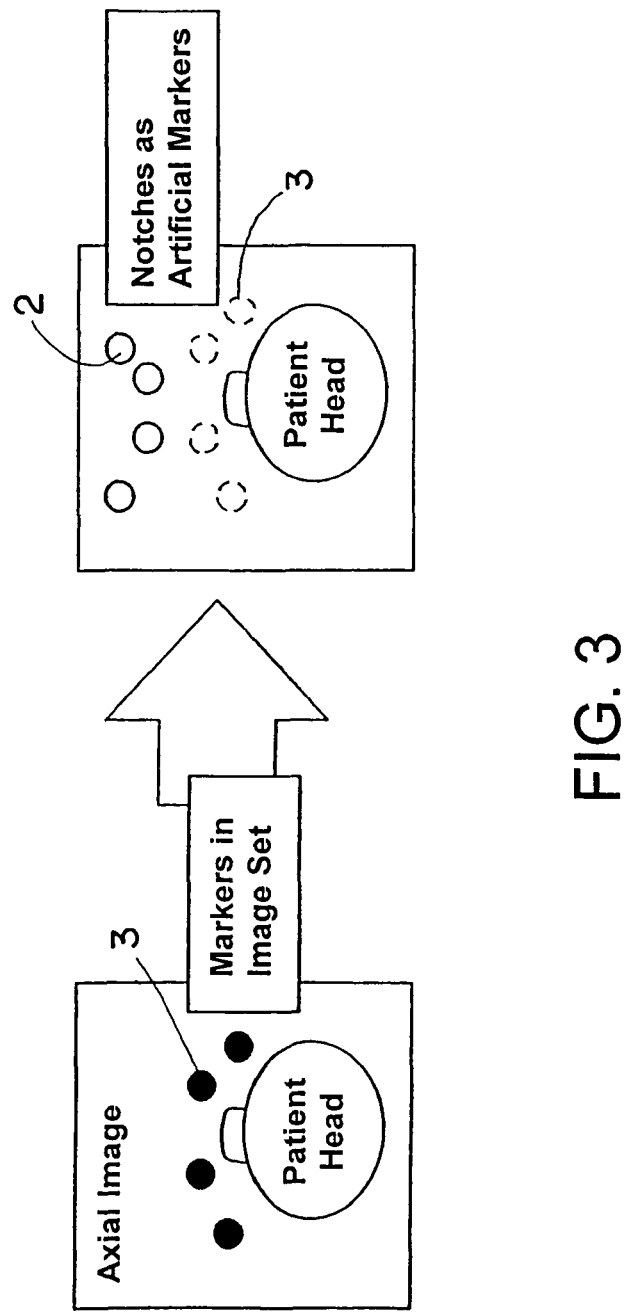
FIG. 3 is an exemplary workflow of a software module for referencing the imaged structure in accordance with the invention.

FIG. 3 shows an exemplary software module, which can detect the registration structure markers 3 in the tomography and calculate a transformation matrix between the detected markers 3 in the image set and the known geometry of the registration structure 10. Thereafter the calculated transformation matrix can be applied to the known position of the notches 2 and, thereby, they may be transformed into the coordinate system of the image set. Artificial markers 2 may be drawn at the exact position of the transformed notches in the image set. Then the registration structure markers 3 can be deleted from the image set by simply blackening them out, and the new series of image sets for the IGS system can be written in a standard image format (e.g. DICOM), which can be read by the IGS system.

Figure 4:
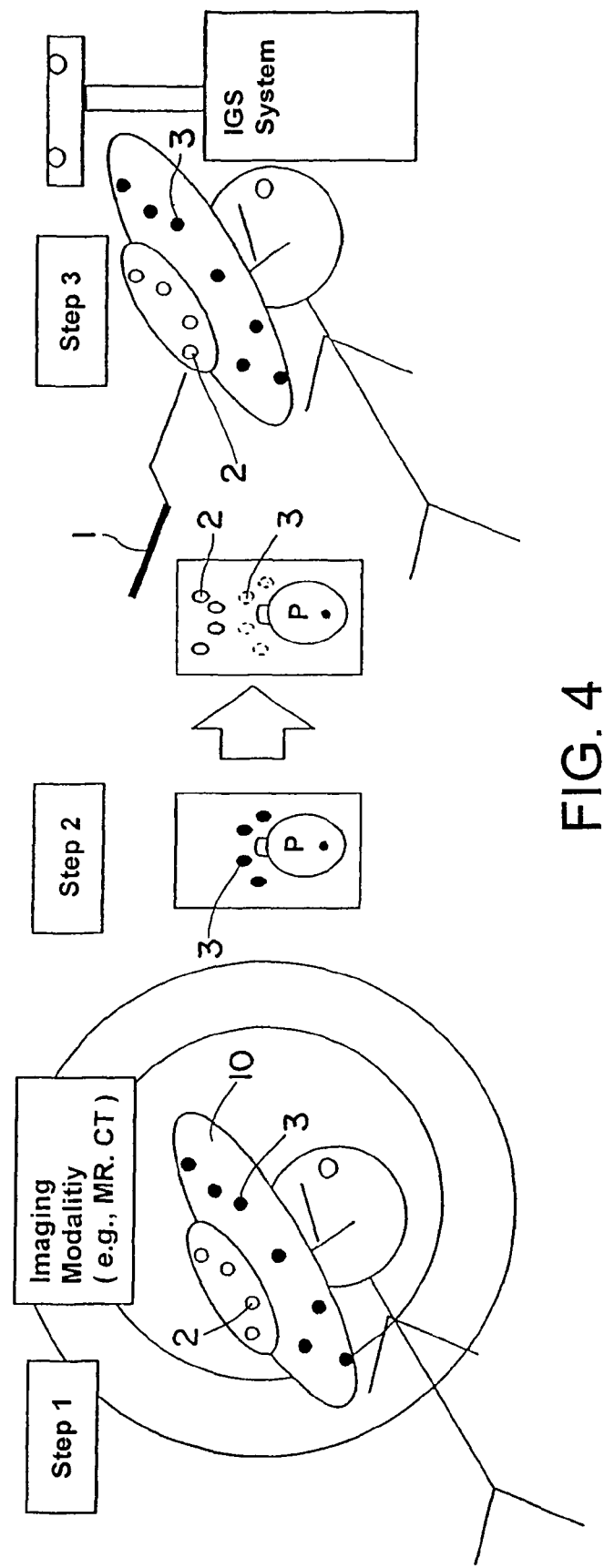
FIG. 4 is a schematic diagram illustrating a method in accordance with the invention.

FIG. 4 shows an exemplary workflow in three steps. Step 1 displays the attachment of the registration structure 10 to the patient during the MRI and/or CT imaging process in such a way that at least half of the markers 3 of the registration structure 10 are imaged. In step 2, the image set is sent to the above described software module for processing. New image sets, containing the artificial markers 2, are then sent to the proprietary IGS system. In step 3, the proprietary IGS system detects artificially drawn markers and asks user to point to the detected markers with a pointer 1 or any other trackable instrument, which also can have markers. The user simply identifies the artificial markers 2 by pointing with his tracked instrument 1 to the notches 2 of the registration structure 10, which will be 'easy-to-reach'.

As the MR/CT scanner is moved and the patient remains in his/her position, the operation is only minimally interrupted.

It is also possible to create a postoperative data record for checking purposes. To do so, the MR/CT scanner may be moved into the operating theater while the patient is still anaesthetized and intubated. The data record, which will then be created anew, is pictorially represented and can be immediately checked by the surgery team. Such a final check-up is an important aid used to confirm that a complete tumor resection has taken place and to exclude acute complications, thereby considerably reducing the risk of having to perform a further operation in case the tumor should grow again. This also helps to reduce costs arising from repeated operations.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for identifying a position of a body structure that is to be registered, wherein a reference structure is attached to the body structure, said reference structure including at least one imaging structure and a plurality of artificial markers arranged at predetermined locations on said reference structure, the artificial markers having a known non-zero spatial offset from the at least one imaging structure, comprising:
   imaging the body structure to obtain a data set describing a relationship between the body structure and the imaging structure;
   creating in the data set, with a computer hardware, artificial marker data corresponding to the locations of the artificial markers on said reference structure, said creating comprising using locations of the imaging structure in the data set and the known non-zero offset from the at least one imaging structure to create the artificial marker data in the data set;
   identifying, using the computer hardware, a position of the artificial markers to a navigation system;
   using the position of the artificial markers and the known relationship between the artificial markers and the imaging structure to identify, using the computer hardware, a position of the body structure in space.

2. The method according to claim 1, wherein imaging the body structure includes imaging at least three markers of the imaging structure.

3. The method according to claim 1, wherein identifying the position of the artificial markers includes using a pointer to identify the artificial markers.

4. The method according to claim 1, wherein using the position of the artificial markers includes:
   calculating a transformation matrix between a known geometry of the reference structure and at least one of the imaging structure and/or the plurality of artificial markers; and
   applying the transformation matrix to the identified position of each artificial marker of the plurality of artificial markers so as to transform the position of the artificial markers into a coordinate system of an image set.

5. The method according to claim 1, further comprising removing, from the data set, data corresponding to the imaging structure.

6. The method according to claim 1, wherein the artificial markers are spaced a fixed distance from the imaging structure.

7. The method according to claim 1, wherein he artificial markers are at least one of a notch or groove.

8. A computer program embodied on a non-transitory computer readable medium for identifying a position of a body structure that is to be registered, wherein a reference structure is attached to the body structure, said reference structure including at least one imaging structure and a plurality of artificial markers arranged at predetermined locations on said reference structure, said artificial markers having a known relationship to the at least one imaging structure and being different from the at least one imaging structure, wherein the program instructs a computer hardware to:
   direct the acquisition of images of the body structure to obtain a data set describing a relationship between the body structure and the imaging structure;
   create in the data set artificial marker data corresponding to locations of the artificial markers on said reference structure, said creating comprising using locations of the imaging structure in the data set and the known non-zero offset from the at least one imaging structure to create the artificial marker data in the data set;
   identify a position of the artificial markers to a navigation system;

use the position of the artificial markers and a known relationship between the artificial markers and the imaging structure to identify a position of the body structure in space.

9. A method for identifying a position of a body structure that is to be registered, wherein a reference structure is attached to the body structure, said reference structure including a first plurality of markers and a second plurality of markers, the first and second plurality of markers arranged at predetermined locations on said reference structure, the second plurality of markers having a known spatial relationship to the first plurality of markers, comprising:

imaging the body structure to obtain a data set describing a relationship between the body structure and the first plurality of markers;

using a trackable pointer to identify, with a computer hardware, a position of the second plurality of markers to a navigation system;

after obtaining the data set of the body structure describing, using the computer hardware, the relationship between the body structure and the first plurality of markers, adding to the data set data corresponding to the second plurality of markers, said adding based on the identified position of the second plurality of markers;

removing from the data set, using the computer hardware, data corresponding to the first plurality of markers;

and identifying, using the computer hardware, a position of the body structure in space using the identified position of the second plurality of markers and the known relationship between the second plurality of markers and the first plurality of markers.

10. The method according to claim 9, wherein imaging the body structure includes using a first imaging modality to obtain the data set, wherein the second set of markers do not image when using the first imaging modality.

* * * * *